United States Patent
Vaughn et al.

(10) Patent No.: US 6,841,510 B2
(45) Date of Patent: Jan. 11, 2005

(54) TREATMENT OF MOLECULAR SIEVES WITH SILICON CONTAINING COMPOUNDS

(75) Inventors: Stephen N. Vaughn, Kingwood, TX (US); John Di-Yi Ou, Houston, TX (US); Jar-Lin Kao, Houston, TX (US); Hsiang-Ning Sun, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/180,483

(22) Filed: Jun. 27, 2002

(65) Prior Publication Data

US 2003/0027712 A1 Feb. 6, 2003

Related U.S. Application Data

(63) Continuation-in-part of application No. 09/505,483, filed on Feb. 16, 2000, now abandoned.

(51) Int. Cl.[7] .............................................. B01J 27/182
(52) U.S. Cl. ......................... 502/214; 502/60; 502/63; 502/64; 502/71; 502/77; 502/85; 502/208
(58) Field of Search ............................ 502/60, 63, 64, 502/71, 77, 85, 208, 214

(56) References Cited

U.S. PATENT DOCUMENTS

| | | | |
|---|---|---|---|
| 4,402,867 A | | 9/1983 | Rodewald |
| 4,452,909 A | | 6/1984 | Yang ............................ 502/69 |
| 4,477,583 A | | 10/1984 | Rodewald |
| 4,683,334 A | * | 7/1987 | Bergna et al. ............... 564/474 |
| 4,849,386 A | | 7/1989 | Wang et al. ................... 502/62 |
| 5,365,003 A | * | 11/1994 | Chang et al. ................ 585/470 |
| 5,756,802 A | | 5/1998 | Li et al. ....................... 558/319 |
| 5,994,603 A | * | 11/1999 | Mohr et al. .................. 585/467 |
| 6,046,371 A | * | 4/2000 | Wu et al. ..................... 585/638 |
| 6,153,798 A | * | 11/2000 | Hidaka et al. ............... 564/479 |

FOREIGN PATENT DOCUMENTS

| | | |
|---|---|---|
| EP | 0 289 691 A1 | 11/1988 |
| EP | 0 893 159 A1 | 1/1999 |

* cited by examiner

*Primary Examiner*—Elizabeth D. Wood

(57) ABSTRACT

This invention is directed to a molecular sieve composition or a catalyst containing molecular sieve which has a relatively high residual silica index, preferably at least about 1.5. The molecular sieve or catalyst can be made by contacting a template-containing molecular sieve with a silicon containing material having an average kinetic diameter that is larger than the average pore diameter of the sieve or catalyst, and heating to leave residual silica at the sieve or catalyst surface. The molecular sieve or catalyst is particularly effective in making an olefin product from an oxygenate feedstock.

46 Claims, 2 Drawing Sheets

Prior Art

US 6,841,510 B2

TREATMENT OF MOLECULAR SIEVES WITH SILICON CONTAINING COMPOUNDS

CROSS REFERENCE TO RELATED APPLICATIONS

This application is a Continuation-In-Part of application Ser. No. 09/505,483, filed Feb. 16, 2000, now abandoned.

FIELD OF THE INVENTION

This invention relates to a molecular sieve having a relatively high residual silica surface content, and the use of the sieve in converting an oxygenate feedstock to an olefin product. In particular, this invention is to a method for converting an oxygenate feedstock to an olefin product by contacting the feedstock with a small pore molecular sieve or catalyst that has been treated such that an external surface is coated with a silicon containing compound and which has subsequently undergone a heat treatment.

BACKGROUND OF THE INVENTION

A molecular sieve is generally a microporous structure composed of either crystalline aluminosilicate, chemically similar to clays and feldspars and belonging to a class of materials known as zeolites, or crystalline aluminophosphates derived from mixtures containing an organic amine or quaternary ammonium salt, or crystalline silicoaluminophosphates which are made by hydrothermal crystallization from a reaction mixture comprising reactive sources of silica, alumina and phosphate. Molecular sieves have a variety of uses. They can be used to dry gases and liquids; for selective molecular separation based on size and polar properties; as ion-exchangers; as catalysts in cracking, hydrocracking, disproportionation, alkylation, isomerization, oxidation, and conversion of oxygenates to hydrocarbons, particularly alcohol and di-alkyl ether to olefins; as chemical carriers; in gas chromatography; and in the petroleum industry to remove normal paraffins from distillates.

Molecular sieves are manufactured by reacting a mixture of several chemical components. One of the components used in the reaction process is a template, although more than one template can be used. The templates are used to form channels or tunnel like structures (also called a microporous structure) within the composition. When the template is removed, an open microporous structure is left behind in which chemical compositions can enter, as long as the chemical compositions are small enough to be able to fit inside the tunnels. Thus a molecular sieve acts to sieve or screen out large molecules from entering a molecular pore structure.

Molecular sieves are particularly desirable for use as catalytic agents. The molecular sieves that act as catalysts have catalytic sites within their microporous structures. Once the template is removed, a chemical feedstock that is small enough to enter into the tunnels can come into contact with a catalytic site, react to form a product, and the product can leave the molecular sieve through any number of the tunnels or pores as long as the product has not become too large to pass through the structure. The pore sizes typically range from around 2 to 10 angstroms in many catalytic molecular sieves.

Template material can be removed from the framework of a molecular sieve by a variety of methods. A preferred method, however, is by calcining or heat treating in an oxygen environment, since calcining under appropriate conditions brings the additional advantage of hardening the molecular sieve. Once the molecular sieve is hardened, it can be more readily transported or more effectively blended with other materials.

In particular, silicoaluminophosphates (SAPOs) have been used as adsorbents and catalysts. As catalysts, SAPOs have been used in processes such as fluid catalytic cracking, hydrocracking, isomerization, oligomerization, the conversion of alcohols or ethers, and the alkylation of aromatics. Notably, the use of SAPOs in converting alcohols or ethers to olefin products, particularly ethylene and propylene, is becoming of greater interest for large scale, commercial production facilities. A description of this process is provided, for example, in U.S. Pat. No. 4,499,327 to Kaiser et al.

In converting oxygenate-containing feedstock to light olefin product, better selectivity to olefin product, as well as away from undesirable by-product, is still needed. It is particularly desirable to obtain product high in ethylene and/or propylene content, while reducing the amount of any one or more of the $C_1$–$C_4$ paraffin by-products.

SUMMARY OF THE INVENTION

In order to provide an olefin product that is relatively high in ethylene and propylene content, this invention provides a molecular sieve having a high concentration of surface silica. Quantitatively, this high concentration is defined by a residual silica index.

Also included in this invention are various embodiments of a method for continuous production of olefin product from an oxygenate-containing feedstock. This invention provides a method of increasing the selectivity of ethylene and/or propylene. In one embodiment, the method comprises treating a template-containing molecular sieve by contacting it with a silicon containing compound followed by the heat treatment of said sieve; and contacting the post-treated sieve with the oxygenate-containing feedstock under conditions effective to convert the oxygenate-containing feedstock to olefin product. In another embodiment, the same processes are applied to a catalyst, which comprises the template-containing molecular sieve and binder. The silicon containing compound should be large enough in molecular kinetic size so as to be prevented from entering the pores of the small pore molecular sieve and catalyst of the invention.

In a preferred embodiment, the template-containing molecular sieve is selected from the group consisting of zeolites, tectosilicates, aluminophosphates and silicoaluminophosphates. Preferably, the template-containing molecular sieve is a crystalline silicoaluminophosphate molecular sieve, and the silicoaluminophosphate molecular sieve is preferably selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, and mixtures thereof.

The current invention involves the contacting of a template-containing small pore molecular sieve or catalyst having an average pore size of less than 5 angstroms with a silicon containing compound. The silicon containing compound is contacted with the template-containing molecular sieve or catalyst in either the liquid phase or a gas phase.

In an embodiment, using a liquid phase contacting variant, the contacting is preferably carried out at a sufficiently high temperature so as to reduce the surface tension-solid interface and reduce the viscosity of the fluid both of which will act to improve the effectiveness of the contacting. As will be appreciated by one skilled in the art, the contacting time and preferred temperature will both be a function of the properties of the silicon containing compound.

In another embodiment, the molecular sieve or catalyst is exposed to the vapor of the silicon containing compound in the vapor phase. Effective conditions for applying the silicon containing compound in the vapor phase will depend upon the vapor pressure characteristics of the silicon containing compound. Silicon containing compounds with boiling points below about 175° C. are preferred. As is well known, the vapor pressure of a compound will increase with increasing temperature. Generally, the rate of application of the silicon containing compound will also increase with increasing partial pressure, thus application at elevated temperatures is preferred.

After either a liquid or vapor contacting treatment, the molecular sieve or catalyst containing the molecular sieve is then subjected to a second treatment by heating to a higher temperature to drive off excess silicon containing compound and decompose any remaining silicon containing compound. In a preferred embodiment, the second treatment is carried out at a temperature of 650° C. These treatments can be carried out post synthesis in a batch reactor. The thus modified sieve/catalyst can be used for the conversion of oxygenates, particularly methanol, into ethylene and/or propylene.

The oxygenate feedstock is preferably selected from the group consisting of methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. More preferably, the oxygenate feedstock is methanol or dimethyl ether.

In order to convert the oxygenate to olefin product, the process is preferably performed at a temperature between 200° C. and 700° C.

BRIEF DESCRIPTION OF THE DRAWINGS

The present invention will be better understood by reference to the Detailed Description of the Invention when taken together with the attached drawings, wherein.

DETAILED DESCRIPTION OF THE INVENTION

Figure 1:
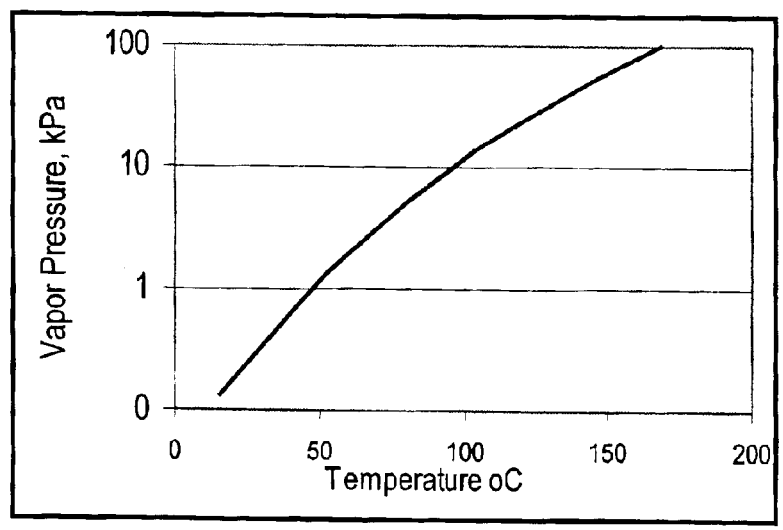
FIG. 1 shows the prior art relationship between vapor pressure and temperature for tetraethyl ortho silicate.

The current invention involves a first treatment of a template-containing small pore molecular sieve/catalyst (i.e., molecular sieve or catalyst comprising the molecular sieve) with a silicon containing compound. The molecular sieve/catalyst can be contacted with a silicon containing compound in either the liquid, vapor or solid phase. A soak temperature and time is selected to improve and enhance the sieve and ultimate catalyst performance by increasing its selectivity to ethylene and/or propylene. The sieve or catalyst is then subjected to a second treatment by heating to higher temperatures to volatilize excess silicon containing compound and to decompose the compound to effect a residual layer of silica formed on the exterior surface of the sieve/catalyst. These catalyst treatment processes can be carried out post synthesis in a batch reactor. The resultant modified catalyst can be used for the conversion of oxygenates, particularly methanol, into an olefin product containing significant quantities of ethylene and/or propylene.

Oxygenates can be converted over small pore molecular sieve and zeolite catalysts with high selectivity to ethylene and/or propylene. Particularly preferred catalysts include SAPO-34, ZSM-34, erionite, SAPO-17, SAPO-18, chabazite, and other similar catalysts. The present invention describes a method by which the selectivity to ethylene and or propylene is enhanced compared to the untreated sieve/catalyst.

The method is accomplished by contacting the template-containing sieve/catalyst with a silicon containing compound. Such a compound is any agent that acts to transfer silicon to an exposed molecular sieve/catalyst material, yet decomposes upon subsequent heating in such a manner that it leaves residual silica on the previously exposed surface. The template-containing molecular sieve/catalyst is generally contacted with a silicon containing compound at a temperature in the range of 20° C. and 300° C. The subsequent heating normally occurs at a temperature in the range of 550° C. and 750° C. A wide variety of silicon containing compounds can be used for this purpose, including but not limited to silicon chloride, silicon acetate, organo-silanes, silicates, siloxanes, silanes, silicon nitride, silanols, silazanes, halogenated silicon compounds and organometallic silicon compounds which may be modified with one or more of the following functional groups; alkyl; vinyl/allyl; acetyl; nitrile; phenyl; phenolic; benzoate; amine; ammonium; ureido; aldhehyde; ketone; alcohol; hydroxyl; carbocylic; esteric; etheric; expoxy; mercapto/thio; and styrl.

For liquid phase application, appropriate silicon containing compounds need a melting point below the point at which significant decomposition takes place and preferably below about 250° C. To be useful in vapor phase applications, the silicon containing compounds should have a vapor pressure above about 2 mbar at a temperature at or below about 250° C. and exhibit negligible decomposition at the temperature at which the vapor is generated and to which the sieve/catalyst is exposed.

The molecule size of the silicon containing substance should be sufficiently large so as to be unable to pass through the catalyst pores and therefore not coat the interior of molecular catalyst sieve. Accordingly, the average kinetic molecular size of the compound must be larger than the small pore size, i.e., greater than 5.0 angstroms. The subsequent heating in the presence of oxygen ("calcination") of the molecular sieve/catalyst after it has been exposed to a silicon containing compound results in a residual layer of silicon oxide being formed on the exterior surface. This calcination yields a molecular sieve/catalyst which demonstrates improved selectivity to light olefins and polyolefins.

The residual silica layer is the result of an enrichment in the surface of silica. Thus, the invention results in an increase in the surface silica, as shown by an increase in the surface Si/Al ratio, which is measured by the residual surface silica index, is defined by the following relationship:

Residual Surface Silica Index $(RSSI)$=[Si/Al (at the surface)]/[Si/Al (within pores)].

The residual surface silica index is preferably at least about 1.5, more preferably at least about 2, and most preferably at least about 3. The residual surface silica index can be determined by any commonly known method of chemical microscopy, such as X-ray Photo Spectroscopy (XPS).

Either liquid or vapor phase deposition of the silicon containing compound can be carried out in batch, semi-batch or continuous mode operations. Batch mode requires sealing an excess of an appropriate silicon containing compound along with either sieve or catalyst in a vessel at a temperature adequate to effect good contacting of the silicon containing compound with the solids in the liquid or vapor phase. Stirring may be used to enhance the contacting. Semi-batch operations require that either the solids or more preferably the silicon containing compound is added continuously to the other component. This mode of operation is expected to be most useful when applied to a contained batch of sieve or catalyst in which a vapor phase silicon containing compound is passed through the vessel. The solids may be stirred, fluidized or otherwise moved about to achieve a more uniform deposition of the silicon containing compound. A continuous process may also be used in which both solids and the silicon containing compound are continuously added to a vessel and product is removed. Particularly suitable apparatus for this mode of operation include fluidized bed, stirred tank, rotary kiln or enclosed conveyor belt. In this embodiment, the silicon containing compound is sprayed onto the solids.

As will be readily understood by one skilled in the art, optimum conditions for practicing the described invention will be a function of 1) the type of silicon containing compound; 2) the physical properties—such as surface tension and fluid viscosity of the silicon containing compound (in the case of liquid-solid contacting); 3) the vapor pressure of the silicon containing compound (in the case of vapor-solids contacting); and 4) the degree of enhanced selectivity desired for a particular process.

With these factors in mind, it is particularly advantageous to operate in the vapor phase mode of contacting at a relatively high vapor pressure, i.e., one that provides effective vaporization to establish a residual silica surface layer. In effect, the silicon containing compound being used will not merely decompose without depositing a desirable level of residual surface silica.

As is known by those of skill in the art, vapor pressure will generally increase with increasing temperature. As an example of this, FIG. 1 shows the increase in vapor pressure of tetraethylorthosilicate as a function of temperature. See, *Handbook of Chemistry and Physics,* 74th Edition, edited by D. R. Lide 1993–1994, CRC Press. For the liquid phase mode of application of the silicon containing compound, elevated temperatures are generally desirable in order to provide a more effective contacting between the liquid silicon containing compound and solid molecular sieve. The application temperature should however be low enough that not too much of the silicon containing compound is lost due to evaporation or decomposition.

Additionally, a suitable hydrocarbon solvent may be optionally used to improve the contacting between the silicon containing compound and the sieve. Suitable solvents include but are not limited to: pentane, hexane, heptane, octane, toluene, petroleum naphtha, petroleum distillates, alcohols and the like.

Extent of modification of the sieve with the silicon containing compound can be controlled by the length of contact time to achieve the desired catalytic properties.

The exposure of the template-containing molecular sieve material to a silicon containing compound and subsequent heating of the exposed molecular sieve material can occur at various points in both the sieve and catalyst processing. In this invention, exposure occurs when a silicon containing compound is applied to the template-containing molecular sieve material. This application can be performed in liquid phase, vapor phase or combinations thereof. The subsequent heat treatment involves heating to decompose the silicon containing compound to form a residual layer of silica only on the external surface of the sieve material. Both pre-treatment and post-treatment molecular sieve materials can be formed into a catalyst using known methods, such as adding a binder material with inert materials and subsequent drying.

In one embodiment, the exposure of the template-containing molecular sieve is performed before the formation of the catalyst. Exposure is performed by applying a silicon containing compound to the template-containing molecular sieve, followed by applying heat. A catalyst can then be formed from the heated sieve. Also, a follow-up calcination may be performed on the catalyst to improve its hardness.

According to this invention, the exposure of the molecular sieve to a silicon-containing compound is performed before the template has been removed from the molecular sieve and before the formation of the catalyst. Exposure is performed by applying a silicon containing compound to the as manufactured template-containing molecular sieve material. The exposed molecular sieve material is heated to form a residual silica layer at the molecular sieve surface. Optionally, the molecular sieve is then heated to remove template (i.e., calcined). The molecular sieve can then be formulated into catalyst. A follow-up calcination may also be performed.

In another embodiment, the exposure to a silicon containing compound and subsequent heating is performed after the formation of the catalyst. After synthesis of the molecular sieve and formation of the catalyst, the catalyst is exposed to a silicon containing compound and heat is applied. Heat can be applied: 1) simultaneously with the removal of the template; 2) before the removal of the template; or 3) after the removal of the template.

Small pore molecular sieves are preferred in this invention. As defined herein, small pore molecular sieves have a pore size of less than about 5.0 Angstroms. Generally, suitable catalysts have a pore size ranging from about 3.5 to about 5.0 angstroms, preferably from about 4.0 to about 5.0 Angstroms, and most preferably from about 4.3 to about 5.0 Angstroms.

Zeolite materials, both natural and synthetic, have been demonstrated to have catalytic properties for various types of hydrocarbon conversion processes. In addition, zeolite materials have been used as adsorbents, catalyst carriers for various types of hydrocarbon conversion processes, and other applications. Zeolites are complex crystalline aluminosilicates which form a network of $AlO_2^-$ and $SiO_2$ tetrahedra linked by shared oxygen atoms. The negativity of the tetrahedra is balanced by the inclusion of cations such as alkali or alkaline earth metal ions. In the manufacture of some zeolites, non-metallic cations, such as tetramethylammonium (TMA) or tetrapropylammonium (TPA), are present during synthesis. The interstitial spaces or channels formed by the crystalline network enable zeolites to be used as molecular sieves in separation processes, as catalyst for chemical reactions, and as catalyst carriers in a wide variety of hydrocarbon conversion processes.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof, but also materials which contain suitable replacement atoms for such silicon and aluminum atoms.

Silicoaluminophosphate molecular sieves are preferred embodiments of this invention. These sieves generally comprise a three-dimensional microporous crystal framework structure of $[SiO_2]$, $[AlO_2]$ and $[PO_2]$ tetrahedral units. The way Si is incorporated into the structure can be determined by $^{29}Si$ MAS NMR. See Blackwell and Patton, *J. Phys. Chem.*, 92, 3965 (1988). The desired SAPO molecular sieves will exhibit one or more peaks in the $^{29}Si$ MAS NMR, with a chemical shift δ(Si) in the range of −88 to −96 ppm and with a combined peak area in that range of at least 20% of the total peak area of all peaks with a chemical shift δ(Si) in the range of −88 ppm to −115 ppm, where the δ(Si) chemical shifts refer to external tetramethylsilane (TMS).

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size ranging from about 3.5 to 5 angstroms, more preferably from 4.0 to 5.0 angstroms. These pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47. Particularly preferable are SAPO-18 and SAPO-34, including the metal containing forms thereof, and mixtures thereof. As used herein, the term mixture is synonymous with combination and is considered a composition of matter having two or more components in varying proportions, regardless of their physical state.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, such as by centrifugation or filtration. The product can also be washed, recovered by the same means and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

The reaction mixture can contain one or more templates. Templates are structure directing agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

Materials which can be blended with the molecular sieve can be various inert or catalytically active materials, or various binder materials to form the "catalyst." These materials include compositions such as kaolin and other clays, various forms of rare earth metals, other non-zeolite catalyst components, zeolite catalyst components, alumina or alumina sol, titania, zirconia, quartz, silica or silica or silica sol, and mixtures thereof. These components are also effective in reducing overall catalyst cost, acting as a thermal sink to assist in heat shielding the catalyst during regeneration, densifying the catalyst and increasing catalyst strength. When blended with non-silicoaluminophosphate molecular sieve materials, the amount of molecular sieve which is contained in the final catalyst product ranges from 1 to 90 weight percent of the total catalyst, preferably 20 to 70 weight percent of the total catalyst.

Additional olefin-forming molecular sieve materials can be mixed with the silicoaluminophosphate catalyst if desired. Several types of molecular sieves exist, each of which exhibit different properties. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. These small pore molecular sieves are described in greater detail in the *Atlas of Zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-34, erionite, and chabazite.

Crystalline aluminosilicate zeolite ZSM-34 is another preferred embodiment used in the present invention for organic compound conversion and particularly hydrocarbon conversion therewith. It belongs to the erionite-offretite family. ZSM-34 is identified by the composition, as synthesized and in anhydrous form, expressed in mole ratios of oxides, as follows:

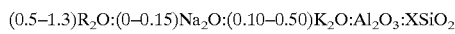

$(0.5–1.3)R_2O:(0–0.15)Na_2O:(0.10–0.50)K_2O:Al_2O_3:XSiO_2$ where R is the organic nitrogen-containing cation derived from choline $[(CH_3)_3NCH_2CH_2OH]$ and X is 8 to 50, preferably 8 to 30 and still more preferably 8 to 20.

ZSM-34 is similar in some respect to offretite or erionite but is distinguished from these zeolites in its capability, after calcination at 1000° F. for at least a period of time sufficient to remove the organic cation, to sorb at least 9.5 weight percent of normal hexane, at ambient temperature and a n-hexane pressure of 20 mm., which is higher than that of any known member of the offretite-erionite family. Further, ZSM-34, as synthesized, contains at least 0.5 mole of $R_2O$ per mole of $Al_2O_3$ in its structure, where R has the significance indicated hereinabove.

The original cations of ZSM-34 can be replaced in accordance with techniques well-known in the art, at least in part, by ion exchange with other cations preferably after calcination. Preferred replacing cations include tetraalkylammonium cations, metal ions, ammonium ions, hydrogen ions, and mixtures of the same. Particularly preferred cations are those which render the zeolite catalytically active, especially for hydrocarbon conversion. These include hydrogen, rare earth metals, aluminum, manganese, and metals of Groups II and VIII of the Periodic Table. The synthesis of zeolites, such as ZSM, by hydrothermal crystallization methods is generally known in the art. See, for example U.S. Pat. No. 4,086,186.

The composition of ZSM-34 can be prepared utilizing materials which supply the appropriate oxide. Such compositions include, for example, sodium aluminate, alumina, sodium silicate, silica hydrosol, silica gel, silicic acid, sodium hydroxide, aluminum sulfate, potassium hydroxide, potassium silicate, and a choline compound such as the halide, i.e. fluoride, chloride or bromide; sulfate, acetate; or nitrate. It will be understood that each oxide component utilized in the reaction mixture for preparing ZSM-34 can be supplied by one or more initial reactants and they can be mixed together in any order. The reaction mixture can be prepared either batchwise or continuously. Crystal size and crystallization time of the ZSM-34 composition will vary with the nature of the reaction mixture employed.

In many instances, it is desired to incorporate the other zeolite materials with another material resistant to the temperature and other conditions employed in organic conversion processes. Such materials include active and inactive materials and synthetic or naturally occurring zeolites as well as inorganic materials such as clays, silica, and/or metal oxides. The latter may be either naturally occurring or in the form of gelatinous precipitates or gels including mixtures of silica and metal oxides. In addition to the foregoing materials, the ZSM-34 zeolite employed herein may be compounded with a porous matrix material, such as alumina, silica-alumina, silica-magnesia, silica-zirconia, silica-thoria, silica-beryllia, silica-titania, as well as ternary combinations, such as silica-alumina-thoria, silica-alumina-zirconia, silica-alumina-magnesia and silica-magnesia-zirconia. Use of such a material in conjunction with ZSM-34 tends to improve the conversion and/or selectively of the catalyst in certain organic conversion processes. Inactive materials suitably serve as diluents to control the amount of conversion in a given process so that products can be obtained economically and in an orderly manner without employing other means for controlling the rate of reaction. Normally, zeolitic materials have been incorporated into naturally occurring clays, e.g., bentonite and kaolin, to improve the crush strength of the catalyst under commercial operating conditions. These materials, i.e., clays, oxides and the like function as binders for the catalyst.

As noted hereinabove, ZSM-34 is useful as a catalyst in organic compound conversion, such as in hydrocarbon conversion. More specifically, the polymerization of compounds containing an olefinic carbon-to-carbon linkage, such as ethylene and propylene, is particularly useful. The process steps and conditions for such conversions are provided in U.S. Pat. Nos. 4,079,095 and 4,079,096 and are incorporated by reference herein. The ZSM-34 catalysts are characterized by high selectivity, under the conditions of hydrocarbon conversion, to provide a high percentage of desired products.

According to this invention, the term molecular sieve refers to crystalline molecular sieve. The term catalyst is used to define the combination of the molecular sieve with other support material such as binder. The catalyst comprises the molecular sieve crystals. The catalyst itself is of a size that can be processed in industrial applications.

The molecular sieve synthesized in accordance with the present method can be used to dry gases and liquids; for selective molecular separation based on size and polar properties; as an ion-exchanger; as a catalyst in cracking, hydrocracking, disproportionation, alkylation, isomerization, oxidation, and conversion of oxygenates to hydrocarbons; as a chemical carrier; in gas chromatography; and in the petroleum industry to remove normal paraffins from distillates. It is particularly suited for use as a catalyst in cracking, hydrocracking, disproportionation, alkylation, isomerization, oxidation, and conversion of oxygenates to hydrocarbons. Most particularly, the molecular sieve is suited for use as a catalyst in the conversion of oxygenates to hydrocarbons.

In its most preferred embodiment as a catalyst in the conversion of oxygenates to hydrocarbons, a feed containing an oxygenate is contacted in a reaction zone of a reactor apparatus with a molecular sieve catalyst at process conditions effective to produce light olefins, i.e., an effective temperature, pressure, WHSV (weight hour space velocity) and, optionally, an effective amount of diluent, correlated to produce light olefins. These conditions are described in detail below. Usually, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions. As used herein, the term reactor includes not only commercial scale reactors but also pilot sized reactor units and lab bench scale reactor units.

Olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of between about 300° C. and 500° C. is preferred.

The process can be carried out in a dynamic bed system or any system of a variety of transport beds rather than in a fixed bed system. It is particularly desirable to operate the reaction process at high space velocities.

The conversion of oxygenates to produce light olefins may be carried out in a variety of large scale catalytic reactors, including, but not limited to, fluid bed reactors and concurrent riser reactors as described in *Fluidization Engineering*, D. Kunii and O. Levenspiel, Robert E. Krieger Publishing Co. NY, 1977, incorporated in its entirety herein by reference. Additionally, countercurrent free fall reactors may be used in the conversion process. See, for example, U.S. Pat. No. 4,068,136 and *Fluidization and Fluid-Particle Systems*, pages 48–59, F. A. Zenz and D. F. Othmo, Reinhold Publishing Corp., NY 1960, the descriptions of which are expressly incorporated herein by reference.

Any standard commercial scale reactor system can be used, including fixed bed or moving bed systems. The commercial scale reactor systems can be operated at a weight hourly space velocity (WHSV) of from 1 $hr^{-1}$ to 1000 $hr^{-1}$. In the case of commercial scale reactors, WHSV is defined as the weight of hydrocarbon in the feed per hour per weight of molecular sieve content of the catalyst. The hydrocarbon content will be oxygenate and any hydrocarbon which may optionally be combined with the oxygenate. The molecular sieve content is intended to mean only the molecular sieve portion that is contained within the catalyst. This excludes components such as binders, diluents, inerts, rare earth components, etc.

The pressure also may vary over a wide range, including autogenous pressures. Preferred pressures are in the range of about 0.5 kPa to about 5 MPa. The foregoing pressures refer to the partial pressure of the oxygenate compounds and/or mixtures thereof.

One or more inert diluents may be present in the feedstock, for example, in an amount of from 1 to 99 molar percent, based on the total number of moles of all feed and diluent components fed to the reaction zone (or catalyst). Typical diluents include, but are not necessarily limited to helium, argon, nitrogen, carbon monoxide, carbon dioxide, hydrogen, water, paraffins, alkanes (especially methane, ethane, and propane), alkylenes, aromatic compounds, and mixtures thereof. The preferred diluents are water and nitrogen. Water can be injected in either liquid or vapor form.

The process may be carried out in a batch, semi-continuous or continuous fashion. The process can be conducted in a single reaction zone or a number of reaction zones arranged in series or in parallel.

The level of conversion of the oxygenates can be maintained to reduce the level of unwanted by-products. Conversion can also be maintained sufficiently high to avoid the need for commercially undesirable levels of recycling of unreacted feeds. A reduction in unwanted by-products is seen when conversion moves from 100 mol % to about 98 mol % or less. Recycling up to as much as about 50 mol % of the feed is commercially acceptable. Therefore, conversions levels which achieve both goals are from about 50 mol % to about 98 mol % and, desirably, from about 85 mol % to about 98 mol %. However, it is also acceptable to achieve conversion between 98 mol % and 100 mol % in order to simplify the recycling process. Oxygenate conversion may be maintained at this level using a number of methods familiar to persons of ordinary skill in the art. Examples include, but are not necessarily limited to, adjusting one or more of the following: the reaction temperature; pressure; flow rate (i.e., WHSV); level and degree of catalyst regeneration; amount of catalyst re-circulation; the specific reactor configuration; the feed composition; and other parameters which affect the conversion.

If regeneration is required, the molecular sieve catalyst can be continuously introduced as a moving bed to a regeneration zone where it can be regenerated, such as for example by removing carbonaceous materials or by oxidation in an oxygen-containing atmosphere. In a preferred embodiment, the catalyst is subject to a regeneration step by burning off carbonaceous deposits accumulated during the conversion reactions.

The oxygenate feedstock comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The method of making the preferred olefin product in this invention can include the additional step of making these oxygenates from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins recovered therefrom. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following examples, which are intended to illustrate specific embodiments within the overall scope of the invention as claimed.

EXAMPLES 1–4

Samples of template-containing, uncalcined, SAPO-34 molecular sieve were treated with successive aliquots of a silicon containing compound—in this case a polydimethylsiloxane, manufactured by Dow Corning Corp under the trade name Dow Corning (R) 200 Fluid ("silicone oil").

Each aliquot was added in excess to that needed to coat the molecular sieve; an oil:sieve ratio of approximately 0.8:1 was used. The mixture of oil and SAPO-34 sieve was heated to 150° C. and held at that temperature for 1 hr to facilitate contacting. The mixture was then heated in an air stream to 650° C. and held for an additional 1 hr to remove the template, drive off the excess silicone oil and decompose the oil associated with the sieve. After the first application of silicone oil a weight increase of approximately 10.45% was measured.

A portion of this silicone oil treated sample was tested for MTO activity in a pulse reactor. This testing was carried out as follows: 10 mg of sieve was sandwiched between two quartz wool plugs in a 4-mm diameter quartz reactor tube. The tube was then inserted into an electrically heated section of a gas chromatograph. Pressure was maintained at 25.0 psig by means off a backpressure regulator and the temperature was maintained at 450±2° C. Helium was passed through the tube at 60 scc/min. One microliter samples of methanol were repeatedly injected onto the catalyst bed and the products of reaction and any unreacted methanol were directed to a gc column for analysis.

As a way of determining the effect of the silicone oil treatments on product selectivity, two ratios were calculated. The $C_2=/C_3=$ ratio indicates the relative selectivity for producing $C_2=$. Generally speaking, a higher $C_2=/C_3=$ ratio is desirable. The second is the $C_{4+}/C_2=$ ratio—this is indicative of the proportion of less desirable products containing 4 or more carbon atoms; thus, a lower value is more desirable.

The procedure outlined above was successively repeated, yielding product molecular sieves that had been treated once (Example 2), twice (Example 3) and three times (Example 4). The performance data is summarized in Table 1, along with the corresponding comparison with a sample that was not contacted with silicone oil (Example 1).

TABLE 1

| Example No. | Number of Silicon Oil Treatments | $C_2=/C_3=$ | $C_4+/C_2=$ |
|---|---|---|---|
| 1 | 0 | 1.02 | 0.38 |
| 2 | 1 | 1.45 | 0.33 |
| 3 | 2 | 1.73 | 0.17 |
| 4 | 3 | 2.50 | 0.12 |

As these results show, the $C_2=/C_3=$ ratio in each of the three treated cases is substantially higher than the untreated case, meaning that there is a substantial increase in ethylene production relative to propylene. The $C_4+/C_2=$ ratio is also substantially decreased, meaning that there is a substantial decrease in undesirable $C_4+$ products relative to the preferred ethylene components.

EXAMPLE 5

As a final example, an uncalcined sample of template-containing SAPO-34 was exposed to the vapors of tetraethylorthosilicate (TEOS) or trimethylethylsilicate (TMES) in a closed system held a room temperature for varying lengths of time up to 28 days. Periodically, a portion of the sample was removed from the container for testing—the remainder of the sample was returned to the closed container. The sample was prepared by first calcining at 650° C. for 1 hr in a flowing air stream. Testing was carried out as described for examples 1–4. The $C_2=/C_3=$ ratio was used in this case to determine changes in selectivity for ethylene production. The results are presented in FIG. 2, no distinction is made between the TEOS or TMES exposed samples since the catalytic performance after exposure is the same in both cases. This figure illustrates the generally improving trend toward higher $C_2=/C_3=$ ratios as the exposure time is increased, achieving nearly double the value after the longest time tested.

Having now fully described this invention, it will be appreciated by those skilled in the art that the invention can be performed within a wide range of parameters within what is claimed, without departing from the spirit and scope of the invention.

What is claimed is:

1. A method of making a molecular sieve comprising:
    providing a template-containing, crystalline silicoaluminophosphate molecular sieve;
    contacting the template-containing molecular sieve with a silicon containing compound; and
    heating the template-containing molecular sieve that has been contacted with the silicon containing compound such that the heated molecular sieve has a residual surface silica index of at least 1.5.

2. The method of claim 1, wherein the heating occurs in an environment having oxygen.

3. The method of claim 1, wherein the healing occurs in an environment containing steam.

4. The method of claim 1, wherein the template-containing molecular sieve has a pore size between 3.5 and 5.0 angstroms.

5. The method of claim 1, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, and mixtures thereof.

6. The method of claim 5, wherein the silicoaluminophosphate molecular sieve is SAPO-18.

7. The method of claim 5, wherein the silicoaluminophosphate molecular sieve is SAPO-34.

8. The method of claim 1, further comprising:
    formulating the template-containing molecular sieve into a catalyst after the heating; and
    calcining the catalyst.

9. The method of claim 1, further comprising:
    formulating the template-containing molecular sieve into a catalyst before the heating.

10. The method of claim 1, wherein the template-containing molecular sieve is contacted with the silicon containing compound at a temperature in the range of 20° C. and 300° C.

11. The method of claim 1, wherein the template-containing molecular sieve is heated to a temperature in the range of 550° C. and 750° C.

12. The method of claim 1, wherein the silicon containing compound is contacted with the template-containing molecular sieve in the vapor phase.

13. The method of claim 1, wherein at least a portion of the silicon containing compound contacting the template-containing molecular sieve is in the liquid phase.

14. The method of claim 1, wherein the silicon containing compound is mixed with a hydrocarbon solvent prior to contacting with the template-containing molecular sieve.

15. The method of claim 1, wherein the heated molecular sieve has a residual surface index of at least 2.

16. The method of claim 15, wherein the heated molecular sieve has a residual surface index of at least 3.

17. A molecular sieve made by the process of claim 16.

18. A crystalline silicoaluminophosphate molecular sieve having a residual surface silica index of at least 1.5.

19. The molecular sieve of claim 18, wherein the residual surface silica index is at least 2.

20. The molecular sieve of claim 19, wherein the residual surface silica index is at least 3.

21. The molecular sieve of claim 18, wherein the molecular sieve has an average pore size of less than or equal to 5 angstroms.

22. The molecular sieve of claim 18, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, end mixtures thereof.

23. The molecular sieve of claim 22, wherein the silicoaluminophosphate molecular sieve is SAPO-18.

24. The molecular sieve of claim 22, wherein the silicoaluminophosphate molecular sieve is SAPO-34.

25. The molecular sieve of claim 22, wherein the silicoaluminophosphate molecular sieve is SAPO-44.

26. A catalyst comprising a crystalline silicoaluminophosphate molecular sieve and a binder, wherein the molecular sieve has a residual surface silica index of at least 1.5.

27. The catalyst of claim 26, wherein the residual surface silica index is at least 2.

28. The catalyst of claim 27, wherein the residual surface silica index is at least 3.

29. The catalyst of claim 26, wherein the molecular sieve has an average pore size of less than or equal to 5 angstroms.

30. The catalyst of claim 26, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, and mixtures thereof.

31. The catalyst of claim 30, wherein the silicoaluminophosphate molecular sieve is SAPO-18.

32. The catalyst of claim 30, wherein the silicoaluminophosphate molecular sieve is SAPO-34.

33. The catalyst of claim 30, wherein the silicoaluminophosphate molecular sieve is SAPO-44.

34. The method of claim 1, wherein the template-containing molecular sieve has an average pore size of less than or equal to 5 angstroms, and wherein the silicon containing compound has a kinetic molecular diameter greater than the average pore size of the template-containing molecular sieve.

35. The method of claim 34, further comprising:
    formulating the template-containing molecular sieve into a formulated catalyst composition comprising the template-containing molecular sieve and binder.

36. The method of claim 35, further comprising:
    calcining the formulated catalyst composition.

37. The method of claim 36, wherein the calcining is effective to remove a template from the formulated catalyst composition.

38. A method of making a molecular sieve comprising:
    providing a crystalline silicoaluminophosphate molecular sieve having an average pore size from 3–15 angstroms;
    contacting the molecular sieve with a silicon containing compound having an average kinetic molecular size larger than the pore size of the molecular sieve; and
    heating the molecular sieve that has been contacted with the silicon containing compound such that the heated molecular sieve has a residual surface silica index of at least 1.5.

39. The method of claim 38, wherein the silicoaluminophosphate molecular sieve has a pore size less than 5.0 Angstroms.

40. The method of claim 38, wherein the silicoaluminophosphate molecular sieve has a pore size between 3.5 and 5.0 Angstroms.

41. The method of claim 38, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, and mixtures thereof.

42. The method of claim 38, wherein the silicoaluminophosphate molecular sieve is SAPO-18.

43. The method of claim 38, wherein the silicoaluminophosphate molecular sieve is SAPO-34.

44. The catalyst of claim 38, wherein the silicoaluminophosphate molecular sieve is SAPO-44.

45. The method of claim 38, wherein the heated molecular sieve has a residual surface index of at least 2.

46. The method of claim 45, wherein the heated molecular sieve has a residual surface index of at least 3.

* * * * *

UNITED STATES PATENT AND TRADEMARK OFFICE
CERTIFICATE OF CORRECTION

PATENT NO. : 6,841,510 B2
DATED : January 11, 2005
INVENTOR(S) : Stephen N. Vaughn et al.

Figure 2:
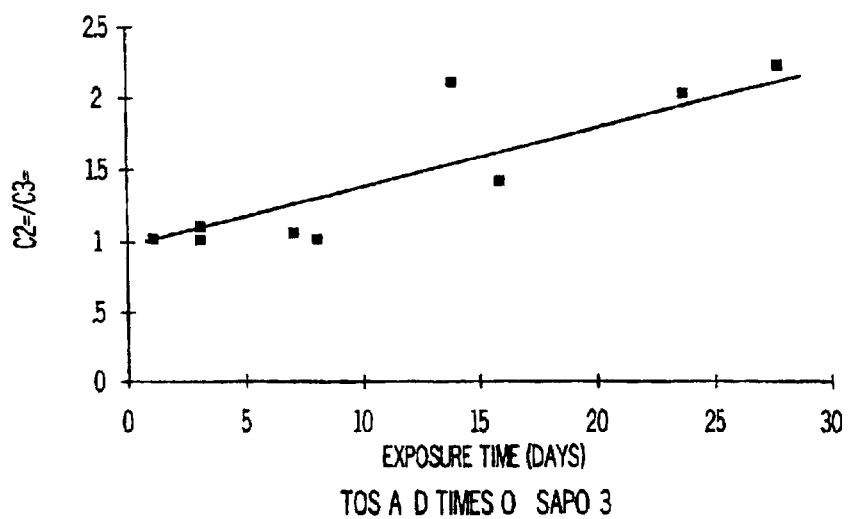
FIG. 2 shows the ethylene to propylene ratios based upon continuing exposure to silicon containing vapor.

It is certified that error appears in the above-identified patent and that said Letters Patent is hereby corrected as shown below:

Drawings,
Fig. 2, replace the caption "TOS A D TIMES O SAPO 3" with -- TEOS AND TMES TIMES ON SAPO 34 --.

Signed and Sealed this

Nineteenth Day of April, 2005

JON W. DUDAS
*Director of the United States Patent and Trademark Office*